US009539277B2

(12) United States Patent
Iacobelli

(10) Patent No.: US 9,539,277 B2
(45) Date of Patent: *Jan. 10, 2017

(54) DEFIBROTIDE FOR USE IN PROPHYLAXIS AND/OR TREATMENT OF GRAFT VERSUS HOST DISEASE (GVHD)

(71) Applicant: GENTIUM S.P.A., Villa Guardia (CO) (IT)

(72) Inventor: Massimo Iacobelli, Milan (IT)

(73) Assignee: GENTIUM S.R.L., Villa Guardia (CO) (IT)

( * ) Notice: Subject to any disclaimer, the term of this patent is extended or adjusted under 35 U.S.C. 154(b) by 0 days.

This patent is subject to a terminal disclaimer.

(21) Appl. No.: 14/616,254

(22) Filed: Feb. 6, 2015

(65) Prior Publication Data

US 2015/0297624 A1 Oct. 22, 2015

Related U.S. Application Data

(63) Continuation of application No. 13/884,102, filed as application No. PCT/IT2010/000451 on Nov. 12, 2010, now Pat. No. 8,980,862.

(51) Int. Cl.

| C07H 21/02 | (2006.01) |
| C07H 21/04 | (2006.01) |
| A61K 31/70 | (2006.01) |
| A61K 31/711 | (2006.01) |
| C12N 15/11 | (2006.01) |
| A61K 31/7088 | (2006.01) |

(52) U.S. Cl.
CPC ......... *A61K 31/711* (2013.01); *A61K 31/7088* (2013.01); *C12N 15/11* (2013.01); *C12N 15/111* (2013.01)

(58) Field of Classification Search
None
See application file for complete search history.

(56) References Cited

U.S. PATENT DOCUMENTS

| 3,770,720 A | 11/1973 | Butti et al. |
| 3,829,567 A | 8/1974 | Butti et al. |
| 3,899,481 A | 8/1975 | Butti et al. |
| 4,649,134 A | 3/1987 | Bonomini |
| 4,693,995 A | 9/1987 | Prino et al. |
| 4,694,134 A | 9/1987 | Ross |
| 4,753,221 A | 6/1988 | Kensey et al. |
| 4,853,221 A | 8/1989 | Elslager |
| 4,985,552 A | 1/1991 | Fedeli et al. |
| 5,081,109 A | 1/1992 | Ulutin |
| 5,116,617 A | 5/1992 | Mantovani et al. |
| 5,223,609 A | 6/1993 | Fedeli et al. |
| 5,624,912 A | 4/1997 | Burcoglu et al. |
| 5,646,127 A | 7/1997 | Lanzarotti et al. |
| 5,646,268 A | 7/1997 | Lanzarotti et al. |
| 5,856,444 A | 1/1999 | Kawakita et al. |
| 5,919,772 A | 7/1999 | Szyf et al. |
| 5,977,083 A | 11/1999 | Burcoglu |
| 6,046,172 A | 4/2000 | Ennio et al. |
| 6,573,372 B2 | 6/2003 | McCall et al. |
| 6,699,985 B2 | 3/2004 | Burcoglu |
| 7,338,777 B2 | 3/2008 | Porta et al. |
| 7,785,797 B2 | 8/2010 | Wohlgemuth et al. |
| 8,551,967 B2 | 10/2013 | Ferro et al. |
| 8,980,862 B2 | 3/2015 | Iacobelli |
| 2002/0142029 A1 | 10/2002 | Porta et al. |
| 2003/0013669 A1 | 1/2003 | Burcoglu |
| 2004/0131588 A1 | 7/2004 | Ferro et al. |
| 2004/0248834 A1 | 12/2004 | Klinman et al. |
| 2005/0059629 A1 | 3/2005 | Gaarde et al. |
| 2005/0196382 A1 | 9/2005 | Vaillant et al. |
| 2005/0215498 A1 | 9/2005 | Eissner et al. |
| 2007/0037144 A1 | 2/2007 | Wohlgemuth et al. |
| 2010/0254938 A1 | 10/2010 | Ferro et al. |
| 2011/0092576 A1 | 4/2011 | Stein et al. |
| 2013/0231470 A1 | 9/2013 | Iacobelli |

FOREIGN PATENT DOCUMENTS

| DE | 19740384 A1 | 3/1999 |
| EP | 0558833 A2 | 9/1993 |
| EP | 0937461 A1 | 8/1998 |
| EP | 1059092 A1 | 12/2000 |
| EP | 1147777 A1 | 10/2001 |
| EP | 1325962 A1 | 7/2003 |
| EP | 1550462 A1 | 7/2005 |
| EP | 1276497 B1 | 11/2005 |
| EP | 1872787 A1 | 1/2008 |
| JP | H02-149527 A | 6/1990 |
| JP | H08-127539 A | 5/1996 |
| JP | 2005-527636 A | 9/2005 |

(Continued)

OTHER PUBLICATIONS

Li, Q., et al., "Involvement of caspase-3 and p38MAPK in allogeneic CD8+T cell—induced apoptosis of vascular endothelial cells," Chinese Journal of Pathophysiology, 2009, vol. 25, issue 9, Published Sep. 15, 2009 pp. 1671-1675.

Biedermann, B.C., "Vascular endothelium and graft-versus-host-disease," Best Practice & Research Clinical Haematology, vol. 21(2): 129-138, 2008.

Karlsson et al., "N-acetyl-L-cysteine promotes T-cell mediated immunity in allogeneic settings in vivo and in vitro," Oral Session 11: Immunotherapy/Experimental Graft-Versus-Host-Disease, 35th Annual Meeting of the European Group for Blood and Marrow Transplantation, Göteborg, Sweden, Mar. 31, 2009.

"Defibrotide—Substance Summary," SIDS 51091757, PubChem Substance, Retrieved from http://pubchem.ncbi.nlm.nih.gov on Mar. 11, 2009, 3 pages.

"Everything you ever wanted to know concerning Oligonucleotides but were afraid to ask," downloaded Jul. 9, 2010 from http://www.auburn.edu/.about.santosr/protocols/OligoProtocols.pdf.

(Continued)

*Primary Examiner* — Sean McGarry
(74) *Attorney, Agent, or Firm* — Cooley LLP

(57) ABSTRACT

Defibrotide for use in prophylaxis and/or treatment of Graft versus Host Disease (GVHD) in humans is disclosed, preferably in hematopoietic stem cell transplantation (HSCT), more preferably allogeneic hematopoietic stem cell transplantation. Graft versus Host Disease of the invention (GVHD) can be acute aGVHD and/or chronic cGVHD, preferably acute.

14 Claims, No Drawings

(56) References Cited

FOREIGN PATENT DOCUMENTS

| WO | WO 87/06235 A1 | 10/1987 |
|---|---|---|
| WO | WO 92/21402 A1 | 12/1992 |
| WO | WO 98/48843 A1 | 11/1998 |
| WO | WO 98/54313 A2 | 12/1998 |
| WO | WO 99/57153 A1 | 11/1999 |
| WO | WO 00/74634 A2 | 12/2000 |
| WO | WO 01/78761 A2 | 10/2001 |
| WO | WO 02/053700 A2 | 7/2002 |
| WO | WO 03/004705 A1 | 1/2003 |
| WO | WO 03/027313 A2 | 4/2003 |
| WO | WO 03/101468 A1 | 12/2003 |
| WO | WO 2004/003166 A2 | 1/2004 |
| WO | WO 2004/028516 A2 | 4/2004 |
| WO | WO 2004/078922 A2 | 9/2004 |
| WO | WO 2005/023273 A1 | 3/2005 |
| WO | WO 2006/094916 A1 | 9/2006 |
| WO | WO 2006/094917 A2 | 9/2006 |
| WO | WO 2006/119619 A1 | 11/2006 |
| WO | WO 2008/000549 A1 | 1/2008 |
| WO | WO 2008/125424 A1 | 10/2008 |

OTHER PUBLICATIONS

"PCT International Search Report dated Jun. 22, 2011 for PCT/IT2010/000451," 2 pgs.

Abdalla, S.A. et al., "Prognostic relevance of microvessel density in colorectal tumours," Oncology Reports, vol. 6, Apr. 16, 1999, pp. 839-842.

Albini, A. et al., "A Rapid in Vitro Assay for Quantitating the Invasive Potential of Tumor Cells," American Association for Cancer Research, vol. 47, Jun. 15, 1987, pp. 3239-3245.

Algire, G., "An Adapation of the Transparent-Chamber Technique to the Mouse," Journal of the National Cancer Institute, vol. 4, No. 1, Aug. 1943, 11 pages.

Andersen, N.F. et al., "Syndecan-1 and angiogenic cytokines in multiple myeloma: correlation with bone marrow angiogenesis and survival," British Journal of Haematology, 2004, vol. 128, pp. 210-217.

Arauz-Pacheco, C. et al., "The treatment of hypertension in adult patients with diabetes," Diabetes Care, vol. 25, No. 1, Jan. 2002, pp. 134-147.

Argoff, C.E. et al., "Diabetic Peripheral Neuropathic Pain: Clinical and Quality-of-Life Issues," Mayo Clinic Proceedings, Supplement, Apr. 2006, vol. 81, No. 4, 34 pages.

Becker et al., "Organikum: organisch-chemisches grundpraktikum" 1990, Deutscher Verlag der Wissenschaften, Berlin, 2 pages.

Belcaro, G. et al., "Fibrinolytic Enhancement in Diabetic Microangiopathy with Defibrotide," Angiology, The Journal of Vascular Diseases, vol. 43, No. 10, Oct. 1992, pp. 793-800.

Belcaro, G. et al., "Laser Doppler Flowmetry and Transcutaneous Oximetry Evaluation in Microangiopathic Diabetic Patients Treated with Defibrotide," Current Therapuetic Research, vol. 46, No. 5, May 1989, pp. 726-732.

Benimetskaya et al., "Angiogenesis alteration by defibrotide: implications for its mechanism of action in severe hepatic veno-occlusive disease," Blood, vol. 112, No. 10, Nov. 15, 2008, pp. 4343-4352.

Berti, F. et al., "Effects of defibrotide on prostacyclin release from isolated rabbit kidneys and protection from post-ischemic acute renal failure in vivo," Eicosanoids, vol. 4, 1991, pp. 209-215.

Bianchi, G. et al., "Defibrotide, a Prostacyclin Releasing Agent, Protects the Rabbit Kidney from Acute Failure," Advances in Prostaglandin, Thromboxane, and Leukotriene Research, vol. 21, 1990, pp. 711-714.

Bonomini, V. et al., "Effect of a new antithrombotic agent (defibrotide) in acute renal failure due to thrombotic microangiopathy," Nephron, vol. 40, No. 2, 1985, pp. 195-200.

Bonomini, V. et al., "Use of Defibrotide in Renal Transplantation in Man," Haemostasis, vol. 16, Supp. 1, 1986, pp. 48-50.

Bostwick, D.G. et al., "Microvessel density in prostate cancer: prognostic and therapeutic utility," Seminars in Urologic Oncology, vol. 16, No. 3, Aug. 1998, pp. 118-123.

Brenchley, "Antagonising angiogenesis in rheumathoid arthritis," Annals of the Rheumatic Diseases, vol. 60, 2001, pp. 71-74.

Burra, P. et al., "Warm Hepatic Ischemia in Pigs: Effects of L-Arginine and Oligotide Treatment," Journal of Investigative Surgery, vol. 14, 2001, pp. 303-312.

Cao, Y., "Tumor angiogenesis and therapy," Biomedicine & Pharmacotherapy, vol. 59, 2005, pp. S340-S343.

Carlo-Stella, C. et al. "Defibrotide significantly enhances peripheral blood progenitor cell mobilization induced by recombinant human granulocyte colony-stimulating factor (rhG-CSF)." Blood. vol. 96. No. 11. Abstract #2374, 2000, p. 553a.

Carlo-Stella, C. et al., "Defibrotide in Combination with Granulocyte Colony-stimulating Factor Significantly Enhances the Mobilzation of Primitive and Committed Peripheral Blood Progenitor Cells in Mice," Cancer Research, vol. 62, Nov. 1, 2002, pp. 6152-6157.

Chapter II Demand for related International Application No. PCT/EP2004/009723, dated Feb. 14, 2005, 10 pages.

Chapter II Demand for related International Application No. PCT/EP2007/054633, dated Apr. 9, 2008, 10 pages.

Chopra et al., "Defibrotide for the treatment of hepatic veno-occlusive disease: results of the Eruopean compassionate-use study," British Journal of Haematology, vol. 111, No. 4, Dec. 2000, pp. 1122-1129.

Chopra et al., "Defibrotide for the treatment of hepatic veno-occlusive disease: results of the European compassionate-use study," British Journal of Haemoyology 111:1122-1129, 2000.

Coccheri, S. et al., "Defibrotide as a Possible Anti-Ischemic Drug," Seminars in Thrombosis and Hemostasis, vol. 22, Supp. 1, 1996, pp. 9-14.

Comandella, M.G. et al., "Functional and morphological effects of defibrotide on renal ischema," Research in Experimental Medicine, vol. 193, 1993, pp. 65-71.

Conde-Knape, K. et al., "Heparan sulfate proteoglycans in experimental models of diabetes: a role for perlecan in diabetes complications," Diabetes/Metabolism Research and Reviews, vol. 17, 2001, pp. 412-421.

Copelan, E.A. et al., "Hematopoietic Stem-Cell Transplantation," N Engl. J. Med. 354:17, Apr. 27, 2006, pp. 1813-1826.

Coppell, J.A. et al., "Hepatic Veno-Occlusive Disease following Stem Cell Transplantation: Incidence, Clinical Course, and Outcome," Biol. Blood Marrow Transplant (2010) 16, pp. 157-168.

Corbacioglu, S. et al., "Defibrotide for Prophylaxis of Hepatic Veno-Occlusive Disease in Paediatric Haemopoietic Stem-Cell Transplantation: An Open-Label, Phase 3, Randomised Controlled Trial," Lancet 379: 1301-1309, 2012.

Corsi, M. et al., "Antiischaemic effect of defibrotide treatment in rat kidney," Drugs Experimental Clinical Research, vol. 19, No. 6, 1993, pp. 261-265.

Corsi, M. et al., "Possible Role of Defibrotide in Endothelial Cell Protection," International Journal of Tissue Reactions, XV(4), 1993, pp. 157-161.

Craddock, C.F. et al., "Antibodies to VLA4 Integrin Mobilize Long-Term Repopulating Cells and Augment Cytokine-Induced Mobilization in Primates and Mice," Blood, vol. 90, No. 12, Dec. 15, 1997, pp. 4779-4788.

Davi, G. et al., "Effects of Defibrotide on Fibrinolytic Activity in Diabetic Patients with Stable Angina Pectoris," Thrombosis Research, vol. 65, No. 2, 1992, pp. 211-220.

Davis, S. "Insulin, Oral Hypoglycemic Agents, and the Pharmacology of the Endocrine Pancreas," Goodman and Gilman's The Pharmacological Basis of Therapeutics, Chapter 60, Section XII, Hormone sand Hormone Antagonists, McGraw-Hill, 2006, pp. 1613-1645.

De Mestre, A.M. et al., "Regulation of Inducible Heparanase Gene Transcription in Activated T Cells by Early Growth Response 1," The Journal of Biological Chemistry, vol. 278, No. 50, Dec. 12, 2003, pp. 50377-50385.

Dempsey, L. et al., "Heparanase expression in invasive trophoblasts and acute vascular damage," Glycobiology, vol. 10, No. 5, 2000, pp. 467-475.

Denne, J.S., "Sample size recalculation using conditional power," Statist. Med. 2001; 20: pp. 2645-2660.

(56) References Cited

OTHER PUBLICATIONS

Dickerson, R.E. et al., "The Anatomy of A-, B- and Z-DNA," Science, vol. 216, No. 4545, 1982, pp. 475-485.
DrugBank, "Showing drug card for Defibrotide (DB04932)," retrieved Jan. 21, 2007 from http://www.drugbank.ca/cgi-bin/getCard.cgi?CARD=DB04932.txt.
Echart, C.L. et al., "The fibrinolytic mechanism of defibrotide: effect of defibrotide on plasmin activity," Blood Coagulation and Fibrinolysis 2009, vol. 20, No. 8, pp. 627-634.
Eissner, G. et al., "Defibrotide, a DNA-based drug, modulates endothelial cell function in multiple ways—impact for transplantation and cancer therapy," Vascular Pharmacoloby, vol. 45, No. 3, Sep. 1, 2006, pp. E152-E153.
Eissner, G. et al., "Fludarabine induces apoptosis, activation, and allogenicity in human endothelial and epithelial cells: protective effect of defibrotide," Blood, Jul. 1, 2002 vol. 100, No. 1, pp. 334-340.
Eissner, G. et al., "Oliogotide, a defibrotide derivative, protects human microvascular endothelial cells against fludarabine-induced activation, damage and allogenicity," Bone Marrow Transplantation, Mar. 2005, 35, pp. 915-920.
Ertault-Daneshpouy, M. et al., "Pericapillary hemorrhage as criterion of severe human digestive graft-versus-host disease," Blood, Jun. 15, 2004, vol. 103, No. 12, pp. 4681-4684.
Esau, Christine C. et al, "Therapeutic potential for microRNAs," Advanced Drug Delivery Reviews, vol. 59, 2007, pp. 101-114.
Falanga, A. et al., "Defibrotide reduces procoagulant activity and increases fibrinolytic properties of endothelial cells," Leukemia (2003);17(8):1636-1642.
Fernandez Pujol, B. et al., "Dendritic cells derived from peripheral monocytes express endothelial markers and in the presence of angiogenic growth factors differentiate into endothelial-like cells," European Journal of Cell Biology, vol. 80, Issue 1, 2001, pp. 99-110.
Ferrara, J.L.M. et al., "Graft-versus-host disease," Lancet 2009: vol. 373, May 2, 2009, pp. 1550-1561.
Ferrero, M.E. et al., "Efficacy of Defibrotide Treatment in Favoring the Function of the Grafted Heart and Kidney in Rats," Transplantation Proceedings, vol. 26, No. 1, Feb. 1994, pp. 251-252.
Ferrero, M.E. et al., "Prostacyclin Release from Endothelial Cells, Induced by Defibrotide Treatment, Favours the Function of Grafted Rat Hearts and Kidneys," International Journal of Tissue Reactions, XIII 4, 1991, pp. 215-218.
Folkman, J. et al., "Isolation of a tumor factor responsible for angiogenesis," Journal of Experimental Medicine, vol. 133, Issue 2, Feb. 1, 1971, pp. 275-288.
Folkman, J. et al., "Switch to the Angiogenic Phenotype during Tumorigenesis," Princess Takamatsu symposia, Jan. 1991, Boca Raton, pp. 339-347.
Fong, D.S. et al., "Diabetic Retinopathy," Diabetes Care, vol. 27, No. 10, Oct. 2004, pp. 2540-2553.
Fontanini, G. et al., "Microvessel count predicts metastatic disease and survival in non-small cell lung cancer," Journal of Pathology, vol. 177, 1995, pp. 57-63.
Frasca, G.M. et al., "Defibrotide Treatment and Disease Progression in Patients with IgA Nephropathy and Impaired Renal Function at Diagnosis," Clinical Drug Investigation, vol. 13, Issue 4, Apr. 1997, pp. 185-191. Abstract Only.
Frasca, G.M. et al., "Effects of defibrotide treatment in patients with IgA nephropathy and reduced renal function," Nephrology Dialysis Transplantation, vol. 11, No. 2, 1996, pp. 392-393.
Giraud-Panis, M-J. et al., "Transplatin-modified oligonucleotides as modulators of gene expression," Pharmacology & Therapeutics, vol. 85, 2000, pp. 175-181.
Goldshmidt, O. et al., "Cell surface expression and secretion of heparanase markedly promote tumor angiogenesis and metastasis," Proceedings of the National Academy of Sciences, vol. 99, No. 15, Jul. 23, 2002, pp. 10031-10036.
Guba, M. et al., "Rapamycin induces tumor-specific thrombosis via tissue factor in the presence of VEGF," Blood, vol. 105, Jun. 1, 2005, pp. 4463-4469.
Guba, M. et al., "Rapamycin inhibits primary and metastatic tumor growth by antiangiogenesis: involvement of vascular endothelial growth factor," Nature Medicine, vol. 8, No. 2, Feb. 2002, pp. 128-135.
Gura, "Systems for Identifying New Drugs are Often Faulty," Science, vol. 278, Nov. 7, 1997, pp. 1041-1042.
Guvakova, M.A. et al., "Phosphorothioate oligodeoxynucleotides bind to basic fibroblast growth factor, inhibit its binding to cell surface receptors, and remove it from low affinity binding sites on extracellular matrix," The Journal of Biological Chemistry, vol. 278, No. 6, Feb. 10, 1995, pp. 2620-2627.
Hames, B.D. et al., "Nucleic Acid Hybridisation," Practical Approach Series, IRL Press, Oxford, 1985, 141 pages.
Han, J. et al., "Endothelial cell injury by high glucose and heparanase is prevented by insulin, heparin and basic fibroblast growth factor," Cardiovascular Diabetology, Aug. 9, 2005, vol. 4, Issue 12, pp. 1-12.
Hanahan, D. et al., "Patterns and emerging mechanisms of the angiogenic switch during tumorigenesis," Cell, vol. 85, Aug. 9, 1996, pp. 353-364.
Hasan, J. et al. "Intra-tumoural microvessel density in human solid tumours," British Journal of Cancer, vol. 86, 2002, pp. 1566-1577.
Hazlehurst, L.A. et al., "Adhesion to fibronectin via b1 integrins regulate p27 kip1 levels and contributes to cell adhesion mediated drug resistance (CAM-DR)," Oncogene, vol. 19, 2000, pp. 4319-4327.
Helmlinger, G. et al., "Interstitial pH and pO2 gradients in solid tumors in vivo: high-resolution measurements reveal a lack of correlation," Nature Medicine, vol. 3, No. 2, Feb. 1997, pp. 177-182.
Hershkoviz, R. et al., "Differential effects of polysulfated polysaccharide on experimental encephalomyelitis, proliferation of autoimmune T cells, and inhibition of heparanase activity," Journal of Autoimmunity, vol. 8, No. 5, Oct. 1995, pp. 741-750. Abstract Only.
Imaginis.com, Centre for Women's Health, "Breast Health, Breast Cancer Glossary of Medical Terms" Retrieved from http://www.imaginis.com/glossary/breast-cancer-glossary-of-medical-terms--11, date unknown.
International Preliminary Report on Patentability for related International Application No. PCT/EP2004/009723, completed May 31, 2005, 7 pages.
International Preliminary Report on Patentability for related International Application No. PCT/EP2006/060304, completed Jun. 8, 2007, 7 pages.
International Preliminary Report on Patentability for related International Application No. PCT/EP2007/054633, completed Sep. 11, 2008, 12 pages.
International Preliminary Report on Patentability for related International Application No. PCT/EP2008/053461, completed Oct. 20, 2009, 11 pages.
International Search Report and Written Opinion for related International Application No. PCT/EP2004/009723, mailed Dec. 22, 2004, 12 pages.
International Search Report and Written Opinion for related International Application No. PCT/EP2006/060304 mailed Apr. 8, 2006, 8 pages.
International Search Report and Written Opinion for related International Application No. PCT/EP2006/060306 mailed Sep. 25, 2006, 8 pages.
International Search Report and Written Opinion for related International Application No. PCT/EP2007/054633 mailed Aug. 24, 2007, 7 pages.
International Search Report and Written Opinion for related International Application No. PCT/EP2008/053461 mailed Oct. 9, 2008, 15 pages.
International Search Report and Written Opinion for related International Application No. PCT/EP2009/053002 mailed Jun. 5, 2009, 11 pages.
Irony-Tur-Sinai, M. et al., "A synthetic heparin-mimicking polyanionic compound inhibits central nervous system inflamma-

(56) References Cited

OTHER PUBLICATIONS tion," Journal of the Neurological Sciences, Jan. 2003, vol. 206, No. 1, Jan. 15, 2003, pp. 49-57. Abstract Only.
Isaji, M. et al, "Tranilast inhibits the proliferation, chemotaxis and tube formation of human microvascular endothelial cells in vitro and angiogenesis in vivo," British Journal of Pharmacology, vol. 122, 1997, pp. 1061-1066.
Japanese Patent Application No. 2013-538335, Official Notice of Rejection mailed Sep. 24, 2014, 6 pages (3 pages English Translation and 3 pages Office Action).
Jeffery, C.J. et al., "The *Escherichia coli* aspartate receptor: sequence specificity of a transmembrane helix studied by hydrophobic-biased random mutagenesis," Protein Engineering, vol. 12, No. 10, 1999, pp. 863-871.
Kainz, C. et al., "Prognostic value of tumour microvessel density in cancer of the uterine cervix stage IB to IIB," Anticancer Research, vol. 15, No. 4, Jul.-Aug. 1995; pp. 1549-1551.
Kaiser, "First Pass at Cancer Genome Reveals Complex Landscape," Science, vol. 313, Sep. 8, 2006, p. 1370.
Kaushansky, K. et al, "Hematopoietic Growth Factors: Understanding Functional Diversity in Structural Terms," The Journal of the American Society of Hematology, Blood, vol. 82, No. 11, Dec. 1, 1993, pp. 3229-3240.
Kelland, "'Of mice and men': values and liabilities of the athymic nude mouse model in anticancer drug development," European Journal of Cancer, vol. 40, 2004, pp. 827-836.
Kerbel, "Human tumor Xenografts as Predictive Preclinical Models for Anticancer Drug Activity in Humans," Cancer Biology & Therapy, vol. 2, No. 4, Suppl. 1, Jul./Aug. 2003, pp. S134-S139.
Khaled, Z. et al., "Multiple mechanisms may contribute to the cellular anti-adhesive effects of phosphorothioate oligodeoxynucleotides," Nucleic Acids Research, vol. 24, No. 4, 1996, pp. 737-745.
Kochar, D.K. et al., "Sodium valproate for painful diabetic neuropathy: a randomized double-blind placebo-controlled study," QJM: An International Journal of Medicine, vol. 97, 2004, pp. 33-38.
Koehl, G.E. et al., "Defibrotide an endothelium protecting and stabilizing drug, has an anti-angiogenic potential in vitro and in vivo," Cancer Biology & Therapy, vol. 6, No. 5, May 2007, pp. 686-690.
Kojima, S. et al., "Enhancement of plasminogen activator activity in cultured endothelial cells by granulocyte colony-stimulating factor," Journal of Cellular Physiology, vol. 138, Jan. 1989, pp. 192-196. Abstract Only.
Kornblum, N. et al., "Defibrotide, a polydisperse mixture of single-stranded phosphodiester oligonucleotides with lifesaving activity in severe hepatic veno-occlusive disease: Clinical outcomes and potential mechanisms of action," Oligonucleotides, vol. 16, 2006, pp. 105-114.
Lee, S.J. et al., "Recognizing and Managing Chronic Graft-Versus-Host Disease," American Society of Hematology (2008) pp. 134-141.
Levidiotis, V. et al., "A synthetic heparanase inhibitor reduces proteinuria in passive heymann nephritis," Journal of the American Society of Nephrology, vol. 15, 2004, pp. 2882-2892.
Levidiotis, V. et al., "Heparanase inhibition reduces proteinuria in a model of accelerated anti-glomerular basement membrane antibody disease," Nephrology, vol. 10, 2005, pp. 167-173.
Levidiotis, V. et al., "Heparanase is involved in the pathogenesis of proteinnuria as a result of glomerulonephritis," Journal of the American Society of Nephrology, vol. 15, 2004, pp. 68-78.
Levidiotis, V. et al., "Increased expression of heparanase in puromycin aminonucleoside nephrosis," Kidney International, vol. 60, 2001, pp. 1287-1296.
Maeshima, Y. et al., "Identification of the Anti-angiogenic Site within Vascular Basement Membrane-derived Tumstatin," The Journal of Biological Chemistry, vol. 276, No. 18, May 4, 2001, pp. 15240-15248.

Marni, A. et al. "Anti-ischemic effect of oligotide treatment in rat kidney: comparison with the effect of nifedipine and isosorbide dinitrate," Transplantation Proceedings, vol. 28, No. 1, Feb. 1996, pp. 301-303.
Marni, A. et al., "Protection of Kidney from Postischemic Reperfusion Injury in Rats Treated with Defibrotide," Transplantation Proceedings, vol. 22, No. 5, Oct. 1990, pp. 2226-2229.
Maxhimer, J.B. et al., "Heparanase-1 gene expression and regulation by high glucose in renal epithelial cells," Diabetes, Jul. 2005, vol. 54, pp. 2172-2178.
McDonald, G.B. et al., "Venocclusive Disease of the Liver after Bone Marrow Transplantation: Diagnosis, Incidence, and Predisposing Factors," Hepatology vol. 4, No. 1, 1984, pp. 116-122.
McDonald, G.B. et al., "Veno-occlusive Disease of the Liver and Multiorgan Failure after Bone Marrow Transplantation: A Cohort Study of 355 Patients," Annals of Internal Medicine, 1993;118:255-267.
Mitsiades, C.S. et al., "Defibrotide (DF) Targets Tumor-Microenvironmental Interactions and Sensitizes Multiple Myeloma and Solid Tumor Cells to Cytotoxic Chemotherapeutics," Blood (ASH Annual Meeting Abstracts), 2004, vol. 104, Abstract 286.
Mitsiades, C.S. et al., "Preclinical Studies in Support of Debribrotide for the Treatment of Multiple Myeloma and Other Neoplasias," Clinical Cancer Research, vol. 15, 2009, pp. 1210-1221.
Mitsiades, C.S. et al., "Preclinical Studies in Support of Defibrotide for the Treatment of Multiple Myeloma and Other Neoplasias," Clin Cancer Res 2009;15(4), Feb. 15, 2009, pp. 1210-1221.
Mitsiades, C.S., "Defibrotide (DF) an Orally Bioavailable Modulator of Myeloma Tumor-Microenvironment Interactions: Molecular Sequetae and Clinical Implications," Blood (ASH Annual Meeting Abstracts), 2006 108: Abstract 3523, Poster Board #-Session: 752-III.
Mitsiades, C.S., et al., "Defibrotide (DF) has anti-neoplastic activity against multiple myeloma: Clinical implications for the incorporation of DF in cytotoxic chemotherapeutic regimes," Blood, vol. 102, No. 11, Nov. 16, 2003, p. 693a, Abstract 2567, Poster Board #-Session: 738-II.
Mondesire, W. et al., "Targeting Mammalian Target of Rapamycin Synergisticallly Enhances Chemotherapy-Induced Cytotoxicity in Breast Cancer Cells," Clinical Cancer Research, vol. 10, Oct. 2004, pp. 7031-7042.
Morabito, A. et al., "Antiangiogenic strategies, compounds, and early clinical results in breast cancer," Critical Reviews in Oncology/Hematology, vol. 49, 2004, pp. 91-107.
Murohara, T. et al., "Cardioprotective actions of oligotide, a single stranded polydeoxyribunucleotide complex, in myocardial ischaemia and reperfusion injury," British Journal of Pharmacology, vol. 117, 1996, pp. 1000-1008.
National Library of Medicine, "Defibrotide"—Medical Subject Heading, 2009 MeSH, MeSH Suplementary Concept Data.
Niada, R., et al., "PGI2-generation and antithrombotic activity of orally administered defibrotide," Pharmacological Research Communications, vol. 14, Issue 10, Nov. 1982, pp. 949-957. Abstract Only.
Orsino, A. et al., "Childhood acute myelomonocytic leukemia (AML-M4) presenting as catastrophic antiphospholipid antibody syndrome," Journal of Pediatric Hematology/Onocology, vol. 26, No. 5, May 2004, pp. 327-330.
Ostrovsky, O. et al., "Genetic variations in the heparanase gene (HPSE) associate with increased risk of GVHD following allogeneic stem cell transplantation: effect of discrepancy between recipients and donors," Blood, Mar. 18, 2010, vol. 115, No. 11, pp. 2319-2328.
Palmer, K.J., et al., "Defibrotide a Review of its Pharmacodynamic and Pharmacokinetic Properties, and Therapeutic Use in Vascular Disorders," Drugs, vol. 45, No. 2, 1993, pp. 259-294.
Parish, C.R. et al., "Heparanase: a key enzyme involved in cell invasion," Biochimica et Biophysica Acta, vol. 1471, 2001, M99-M108.
Parish, C.R. et al., "Treatment of central nervous system inflammation with inhibitors of basement membrane degradation," Immunology and Cell Biology, vol. 76, No. 1, Feb. 1998, pp. 104-113.

(56) References Cited

OTHER PUBLICATIONS

PCT International Preliminary Report on Patentatbility for related International Application No. PCT/EP2006/060306, issued Sep. 12, 2007, 1 page.

Pellegatta, F. et al., "The anti-ischemic drugs defibrotide and oligotide analogously inhibit leukocyte-endothelial cell adhesion in vitro," Transplant International, vol. 9, Suppl. 1, 1996, pp. S420-S424.

Persengiev, S.P. et al., "Nonspecific, concentration-dependent stimulation and repression of mammalian gene expression by small interfering RNAs (siRNAs)," RNA, vol. 10, 2004, pp. 12-18.

Pescador, R. et al., "An Integrated View of the Activities of Defibrotide," Seminars in Thrombosis and Hemostasis, vol. 22, Suppl. 1, 1996, pp. 71-75.

Podar, K. et al., "The pathophysiologic role of VEGF in hematologic malignancies: therapeutic implications," Blood, vol. 105, No. 4, Feb. 15, 2005, pp. 1383-1395.

Prosper, F. et al., "Mobilization and Homing of Peripheral blood Progenitors is Related to Reversible Downregulation of alpha4Beta1 Integrin Expression and Function," The American Society for Clinical Investigation, Inc., vol. 101, No. 11, Jun. 1998, pp. 2456-2467.

PureLink Brochure, "Nucleic Acid Purification" Invitrogen, 2007, 8 pages.

Richardson et al., "Defibrotide for the Treatment of Severe Hepatic Veno-Occlusive Disease and Multiorgan Failure after Stem Cell Transplanation: A Multicenter, Randomized, Dose-Finding Trial," Biol Blood Marrow Transplant 16: 1005-1017, 2010.

Richardson et al., "Multi-institutional use of defibrotide in 88 patients after stem cell transplantation with severe veno-occlusive disease and multisystem organ failure: response without significant toxicity in a high-risk population and factors predictive of outcome," Blood 100(13):4337-4343, 2002.

Richardson, P.G. et al., "Multi-institutional use of defibrotide in 88 patients after stem cell transplantation with severe veno-occlusive disease and multi-system organ failure: response without significant toxicity in a high risk population and factors predictive of outcome," Blood, vol. 100, No. 13, Dec. 15, 2002, pp. 4337-4343.

Richardson, P.G. et al., "Treatment of severe veno-occlusive disease with defibrotide: compassionate use results in response without significant toxicity in a high-risk population," Blood, vol. 92, No. 3, Aug. 1, 1998, pp. 737-744.

Rowlings, P.A. et al., "IBMTR Severity Index for grading acute graft-versus-host disease: retrospective comparison with Glucksberg grade," British Journal of Haematology, 1997, 97, pp. 855-864.

Ruutu, T et al., "Diagnostic criteria for hematopoietic stem cell transplant-associated microangiopathy: results of a consensus process by an International Working Group," haematologica/the hematology journal, 2007; 92(1):95-100.

Schroder, "Defibrotide protects endothelial cells, but not L929 tumour cells, from tumour necrossis factor-alpha-mediated cytotoxicity," Journal of Pharmacy and Pharmacology, vol. 47, 1995, pp. 250-252.

Simizu, S. et al., "Heparanase as a molecular target of cancer chemotherapy," Cancer Science, vol. 95, No. 7, Jul. 2004, pp. 553-558.

Staton, C.A. et al., "Current methods for assaying angiogenesis in vitro and in vivo," International Journal of Experimental Pathology, vol. 85, 2004, pp. 233-248.

Stephan, S. et al., "Effect of Rapamycin Alone and in Combination with Antiangiogenesis Therapy in an Orthotopic Model of Human Pancreatic Cancer," American Association for Cancer Research, vol. 10, Oct. 15, 2004, pp. 6993-7000.

Sun, H.C. et al., "Microvessel density of hepatocellular carcinoma: its relationship with prognosis," Journal of Cancer Research and Clinical Oncology, vol. 125, 1999, pp. 419-426.

Tai, BC et al., "Competing risks analysis of patients with osteosarcoma: a comparison of four different approaches," Statis. Med. 2001; 20:661-684.

Tamsma, J.T. et al., "Expression of glomerular extracellular matrix components in human diabetic nephropathy: decrease of heparan sulphate in the glomerular basement membrane," Diabetologia, vol. 37, 1994, pp. 313-320.

Trichon, B.H. et al., "Acute coronary syndromes and diabetes mellitus," Diabetes and Vascular Disease Research, vol. 1, Issue 1, May 2004, pp. 23-32.

Van Den Born, J. et al., "Distribution of GBM heparan sulfate proteoglycan core protein and side chains in human glomerular diseases," Kidney International, vol. 43, 1993, pp. 454-463.

Van 'T Veer, L.J. et al., "Gene expression profiling predicts clinical outcome of breast cancer," Nature, vol. 415, Jan. 31, 2002, pp. 530-536.

Verheul, H.M.W. et al., "Are tumours angiogenesis-dependent?," Journal of Pathology, vol. 202, 2004, pp. 5-13.

Vermuelen, M. et al., "Role of Adhesion Molecules in the Homing and Mobilization of Murine Hematopoietic Stem and Progenitor Cells," Blood, vol. 92, No. 3, Aug. 1, 1998, pp. 894-900.

Vingolo, E.M., et al., "Treatment of nonproliferative diabetic retinopathy with Defibrotide in noninsulin-dependent diabetes mellitus: A pilot study," Acta Opthalmologica, vol. 77, 1999, pp. 315-320.

Vlodaysky, I. et al., "Mammalian heparanse: Gene cloning, expression and function in tumor progression and metastasis," Nature Medicine, vol. 5, No. 7, Jul. 1999, pp. 793-802.

Vlodaysky, I. et al., "Molecular properties and involvement of heparanase in cancer metastasis and angiogenesis," The Journal of Clinical Investigation, vol. 108, No. 3, Aug. 2001, pp. 341-347.

Voskoglou-Nomikos, T. et al., "Clinical Predictive Value of the in Vitro Cell Line, Human Xenograft, and Mouse Allograft Preclinical Cancer Models," Clinical Cancer Research, vol. 9, Sep. 15, 2003, pp. 4227-4239.

Weidner, N. et al., "Tumor angiogenesis: a new significant and independent prognostic indicator in early-stage breast carcinoma," Journal of the National Cancer Institute, vol. 84, No. 24, Dec. 16, 1992, pp. 1875-1887.

Xiangming, C. et al., "Angiogenesis as an unfavorable factor related to lymph node metastasis in early gastric cancer," Annals of Surgical Oncology, vol. 5, No. 7, 1998, pp. 585-589.

Yang, Y. et al., "Heparanase promotes the spontaneous metastasis of meloma cells to bone," Blood, vol. 105, No. 3, Feb. 1, 2005, pp. 1303-1309.

DEFIBROTIDE FOR USE IN PROPHYLAXIS AND/OR TREATMENT OF GRAFT VERSUS HOST DISEASE (GVHD)

The present invention relates to defibrotide for use in prophylaxis and/or treatment of Graft versus Host Disease (GVHD) in humans, preferably in hematopoietic stem cell transplantation (HSCT), more preferably allogeneic hematopoietic stem cell transplantation. Graft versus Host Disease of the invention (GVHD) can be acute aGVHD and/or chronic cGVHD, preferably acute.

STATE OF THE ART

Graft versus Host Disease (GVHD) is the most frequent complication after allogeneic haematopoietic stem cell transplantation (HSCT). GVHD can occur despite aggressive immunosuppressive prophylaxis even when the donor is a perfectly matched (HLA identical) sibling. It is a consequence of interactions between antigen presenting cell of recipient and mature-cell of donor.

Traditionally, GvHD is regarded as an epithelial cell disease. The three organs mainly involved in acute GvHD are skin, gastrointestinal tract and liver. All of them share the common feature of presenting a barrier to the 'environment' of the host. Chronic GvHD similarly attacks barrier tissues. In the chronic sicca syndrome of the eye, the oral, intestinal or genital mucosal compartments, as well as in bronchiolitis obliterans, the epithelial barrier of the mucosa is involved. Furthermore, GvHD is often considered as a single disease, split into two phases: an acute phase of GvHD occurring early after HSCT, and a chronic phase in which GvHD appears later in the course of transplantation.

Finally, in the traditional view, GvHD is cytokine-triggered. Damage induced by the conditioning preparative regimen used before transplantation and infections causes the release of diverse cytokines which are responsible for an inflammatory process, enhancing the GvHD reaction.

Defibrotide, a polydisperse mixture of single-stranded oligonucleotides, has a protective effect on activated endothelial cells. Preclinical studies revealed that defibrotide protects these cells against chemotherapy-induced cell death and activation, and downregulates the gene expression, protein level and activity of endothelial cell-triggers like heparanase. Defibrotide reduces procoagulant activity and increases fibrinolytic properties of stimulated endothelial cells without exacerbating systemic bleeding. Clinical studies of defibrotide in patients with severe hepatic Veno-Occlusive Disease (VOD) following HSCT have reported complete resolution in 36 to 50% of patients, and Day+100 survival in 35 to 42%. The prophylactic role of defibrotide has not been studied prospectively, but appears promising. We evaluated the efficacy and safety of defibrotide in preventing VOD against standard practice (no VOD prophylaxis) in a high-risk pediatric HSCT population.

DEFINITION

The term defibrotide identifies a polydeoxyribonucleotide that is obtained by extraction from animal and/or vegetable tissues but which may also be produced synthetically; the polydeoxyribonucleotide is normally used in the form of an alkali-metal salt, generally a sodium salt, and generally has a molecular weight of 13 to 30 kDa (CAS Registry Number: 83712-60-1). Preferably, defibrotide is obtained according to U.S. Pat. Nos. 4,985,552 and 5,223,609 and/or presents the physical/chemical characteristics described in the same U.S. Pat. Nos. 4,985,552 and 5,223,609, herein incorporated by reference. More in particular, defibrotide is a mixture of polydeoxyribonucleotides having formula of random sequence:

$$P1-5, (dAP)_{12-24}, (dGP)_{10-20}, (dPp)_{13-26}, (dCP)_{10-20}$$

wherein
P=phosphoric radical,
dAp=deoxyadenylic monomer,
dGp=deoxyguanylic monomer,
dTp=deoxythymidinic monomer,
dCp=deoxycytidynic monomer.
and/or shows the following chemical/physical characteristics:

Electrophoresis=homogeneous anodic mobility, and/or extinction coefficient, $E_{1\ cm}^{1\%}$ at 260±1 nm nm=220±10, and/or $E_{230}/E_{260}$=0.45±0.04, and/or coefficient of molar extinction (referred to phosphorous) $\epsilon(P)$=7.750±500, and/or rotatory power $[\alpha]_D^{20°}$=−53°±6; and/or reversible hyperchromicity, indicated as % in native DNA and/or h=15±5.

The term humans identifies any subject as adult subjects and pediatric population, wherein with the term pediatric population is intended the part of population from birth to eighteen (18) years old.

The term aGVHD identifies acute Graft versus Host Disease;

The term cGVHD identifies chronic Graft versus Host Disease; and

The term allogenic referred to hematopoietic stem cell transplantation (HSCT) identifies transplant from an healthy subject to a (patient) recipient.

DESCRIPTION OF THE INVENTION

The present invention refers to defibrotide for use in prophylaxis and/or treatment of Graft versus Host Disease (GVHD) in humans, preferably in hematopoietic stem cell transplantation (HSCT). Graft versus Host Disease of the invention (GVHD) can be acute aGVHD and/or chronic cGVHD, preferably acute.

According to the invention, defibrotide can be administered to humans before and/or after hematopoietic stem cell transplantation (HSCT).

We have recently performed an international, randomized, controlled, open-label trial, wherein we compared defibrotide (Gentium S.p.A.) prophylaxis with no prophylaxis in pediatric HSCT patients at high risk for developing VOD. The primary endpoint was the incidence of VOD by Day+30 post-HSCT, adjudicated by a blinded, independent review committee. Secondary endpoints included graft-versus-host disease (GVHD), VOD-related organ failure and mortality.

A total of 356 patients met the inclusion criteria and gave informed consent to be randomized to the i.v. defibrotide arm (n=180) or the control arm (n=176). VOD was reported in 22 patients (12%) in the defibrotide arm and in 35 patients (20%) in the control arm (competing risk, P=0.05; Kaplan-Meier, P=0.05). The incidence and severity of acute GVHD were significantly reduced (P=0.005 and P=0.003, respectively) in the allogeneic recipients. VOD-associated organ failures were lower in the defibrotide arm with a significant reduction in the incidence of renal failure (1% vs. 6%, P=0.02). A significantly higher Day+100 mortality was observed in patients with VOD (25% vs. 6%; P<0.001). Although mortality after VOD diagnosis was lower in the defibrotide arm (4 vs. 10 patients, P=0.1), overall mortality was similar in the two arms. There was no difference in the incidence of adverse events between arms (87% vs. 88%).

Defibrotide reduced the incidence of VOD by 40%, as well as the incidence and severity of acute GVHD, and has a good safety profile. (ClinicalTrials.gov number, NCT00272948.)

Methods:

Study Design

This study was a phase 3, multicenter, randomized trial, supported Gentium S.p.A. The study protocol and patient consent form were approved by the research ethics committees of the participating centers and written informed consent was obtained from patients and/or their legal representatives prior to study entry.

Treatment assignments were generated by a central data manager with a computer algorithm accessing a randomization sequence. Randomization was 1:1, stratified by center and the diagnosis of osteopetrosis. An independent data and safety monitoring board (DSMB) of three expert hematologists and a statistician reviewed the safety and mortality data at predetermined intervals. A blinded independent review committee (IRC) of three expert hematologists reviewed and adjudicated diagnosis for all suspected and documented VOD cases. An independent statistician performed the data analysis.

Eligible patients were aged <18 years with myeloablative conditioning for allogeneic or autologous HSCT, who had at least one risk factor for VOD: pre-existing liver disease, second myeloablative HSCT, allogeneic HSCT for leukemia beyond the second relapse, conditioning with busulfan and melphalan, previous treatment with GO, and diagnoses of inherited MAS, adrenoleukodystrophy, or osteopetrosis.

Treatment

For patients randomized to the open-label defibrotide arm, the study drug was administered daily at 25 mg per kilogram of body weight per day in four divided intravenous infusions. Defibrotide prophylaxis started on the same day as the pre-transplant conditioning regimen and was continued until Day+30 or, if discharged from hospital before Day+30, for a minimum of 14 days. Patients in the control arm received no prophylaxis against VOD. Treatment with systemic t-PA, therapeutic-dose heparin or other antithrombotics was not permitted. Ursodiol was permitted.

Patients in either arm who developed VOD received treatment with defibrotide at 25 mg per kilogram per day until complete resolution of all symptoms or death.

Outcome Measures

The primary endpoint was the incidence of VOD by Day+30. VOD was assessed by the Investigator according to modified Seattle criteria, defined as the presence of two or more criteria: bilirubin >2 mg per deciliter (>34 µmol per liter), hepatomegaly, ascites, and/or unexplained weight gain >5% from baseline (modified from >2% weight gain in the original Seattle criteria[2]).

Laboratory parameters, including bilirubin, were measured at baseline (before conditioning) and at least weekly post transplant. All patients underwent abdominal ultrasonography at baseline and after transplant, when VOD was clinically suspected, to confirm presence of hepatomegaly and ascites. The blinded ultrasound reports and clinical data were sent to the IRC for adjudication of suspected and diagnosed VOD cases. The IRC assessments were used in the primary efficacy analysis.

The secondary and exploratory efficacy parameters included:

(a) The incidence and severity of GVHD (International Bone Marrow Transplant Registry index) by Day+100 and Day+180.

(b) MOF and mortality by Day+100; although this study was not powered to assess MOF or mortality, these endpoints were analyzed together using a composite scoring system for the assessment of VOD severity. This system assigned one point for each organ failure in patients with VOD: respiratory failure (oxygen requirement and/or ventilator dependence), renal failure (the doubling of baseline creatinine level and/or dialysis dependence) and encephalopathy; five points were assigned for death (regardless of cause of death). Patients without VOD were assigned zero. Each composite score component was also analyzed individually.

(c) The incidence of transplant-associated microangiopathy (TAM)[31] by Day+180.

Adverse events were recorded until Day+180 and coded using MedDRA terms.

Statistical Analysis

Analyses were performed as specified in the protocol and statistical analysis plan. The sample size was estimated based on the primary endpoint (VOD incidence by Day+30). VOD rates were estimated at 30% in the control arm and 15% in the defibrotide arm. Assuming a one-sided level of significance at 0.025, power of 80%, and a 10% dropout rate, 135 patients per arm were required. Because the incidence of VOD in children was unclear when the study was designed, the protocol incorporated a planned adaptive interim analysis, following the algorithm of Denne, to be reviewed by an independent DSMB when 120 patients per arm reached the Day+30 primary endpoint. The DSMB recommended to increase the sample size to a total of 360 randomized patients.

All data analyses were performed on the intent-to-treat (ITT) population, which included all patients with informed consent randomized into the study. Comparison against the defibrotide arm for the primary efficacy analysis was performed using a cumulative competing risk approach by Kalbfleisch and Prentice as discussed in Tai et al., where death not due to VOD, discontinuing the study due to an adverse event, and receipt of second transplant due to transplant failure, were considered competing risks. A supportive analysis was also performed using the log-rank test with Kaplan-Meier estimates of VOD rate, where patients not experiencing VOD were censored at Day+30, last known follow-up, or at the time of competing risk, whichever was earlier. A secondary per protocol (PP) analysis was also planned, excluding prematurely withdrawn ITT patients and ITT patients with serious protocol violations.

The secondary efficacy analyses on the incidence and severity of GVHD were analyzed using the Z-test for proportions and the two-sample Wilcoxon rank sum test, respectively. Patients with no GVHD were assigned a severity value of 0.

The analysis on the VOD composite score was performed using an exact Wilcoxon's test with a two-sided 5% level of significance.

Each composite score component was analyzed using the chi-square test. Kaplan-Meier distributions of time to death by Day+100 for each study arm were compared using the log-rank test, where surviving patients were censored at Day+100 or last known follow-up, whichever was earlier.

The safety population was defined for the defibrotide arm as all recipients of at least one dose of study drug, and for the control arm as all assigned patients. Safety parameters were assessed using frequency tables for serious and non-serious adverse events (AEs), laboratory tests, and survival up to Day+180, where survival is defined as the time in days between HSCT and death from any cause.

Results:
Patient Characteristics

Between January 2006 and January 2009, 360 patients were randomized to the study in 28 centers in 11 countries in Europe. In the defibrotide arm, 181 patients were randomized, one in error (without consent), resulting in 180 patients in the ITT population. In the control arm, 179 patients were randomized, three in error (without consent), resulting in 176 patients in the ITT population.

The mean age of the study population was 6.6 years. Patients were evenly distributed with respect to age and gender across the study arms (Table 1). The primary diseases, type of donor, type of graft, and incidence of risk factors for VOD were similar between arms. Patients randomized to the defibrotide arm received study drug for a mean duration of 32.4 days (median, 35.0). When defibrotide was used for treatment of VOD, the mean duration of therapy was 28.7 days (median, 23.0) for the defibrotide arm and 21.7 days (median, 18.5) for the control arm. The number of patients using concomitant ursodiol was similar between arms.

VOD Incidence:

The incidence of VOD was reduced by 40% in the defibrotide arm compared with the control arm. Analysis of the ITT population showed a significantly lower incidence of VOD by Day+30 in the defibrotide arm versus the control arm (cumulative incidence, 12% vs. 20%, respectively, according to modified Seattle criteria; competing risk, P=0.05; Kaplan-Meier, P=0.05; Table 2). Analysis of the PP population also showed statistically significant results (competing risk, P=0.02; Kaplan Meier, P=0.02).

To explore consistency of results across different criteria, an additional subset analysis was performed applying Baltimore criteria, where bilirubin >2 mg per deciliter (>34 μmol per liter) is required for VOD diagnosis, with two of other three criteria, hepatomegaly, ascites or weight gain >5%. We identified fewer VOD cases with Baltimore criteria (7% in the defibrotide arm, 13% in the control arm; P=0.09; Table 2). While not significant, these data are consistent with the 40% reduction in VOD observed with modified Seattle criteria.

Effect of Defibrotide on GVHD

The patients who received defibrotide prophylaxis experienced a significantly lower incidence and severity of aGVHD by Day+100. In allogeneic HSCT recipients from the ITT population, the incidence and severity (Grades 1 to 4) of aGVHD were significantly lower in the defibrotide arm than in the control arm (P=0.005 and P=0.003, respectively), even when Grade 1 aGVHD was excluded (Table 3). There was no difference in the incidence of chronic GVHD (cGVHD) by Day+180 between study arms.

Despite its protective effects against aGVHD, defibrotide did not interfere with the desirable graft versus leukemia effect. The combined Day+100 relapse rates of acute lymphoblastic leukemia, acute myeloid leukemia, other leukemias and myelodysplastic syndromes were 6% for the defibrotide arm versus 8% for the control arm, and combined Day+180 relapse rates were 7% and 10%, respectively.

VOD-Associated MOF and Death:

To assess the effects of defibrotide on the severity of VOD, a pre-specified composite scoring system was used to quantify VOD-associated MOF and death up to Day+100. Overall, the defibrotide arm had fewer VOD-associated organ failures and deaths, resulting in a statistically significant reduction of scores (Wilcoxon test, P=0.03) in the ITT population (Table 4). Specifically, the defibrotide arm showed a statistically significant lower incidence of renal failure compared with the control group (1% vs. 6%; P=0.02). Severe VOD-associated MOF by Day+100 was significantly higher in patients who fulfilled Baltimore criteria (60% vs. 32%; chi-square test, P=0.04).

VOD-associated mortality at Day+100 was lower in the defibrotide arm than the control arm (2% and 6%, respectively), but these results were not statistically significant (Table 4). Overall mortality was similar in the two arms when assessed at Day+100 and Day+180

Mortality was significantly higher in patients with VOD at Day+100 than in those without VOD (25% vs. 6%, respectively; P<0.0001).

Overall, most fatal AEs were in the categories "Neoplasms, Malignant and Unspecified" (7% and 8% in the defibrotide and control arms, respectively), and "Infections and Infestations" (3% and 6%, respectively).

TAM

There was no difference in the incidences of TAM (3% and 4% in the defibrotide and control arms, respectively) by Day+180.

Safety

The safety population included 177 patients of the defibrotide arm and all 176 patients in the control arm. The incidences of AEs (Table 5), and of serious adverse events (SAEs) and events leading to study discontinuation were similar between arms. A total of 207 SAEs were reported in 108 patients assigned to the defibrotide arm and 231 were reported in 103 control patients. Although the most common AE considered by the Investigator to be possibly, likely or certainly related to defibrotide was hemorrhage, the incidence of hemorrhage was similar between arms.

Discussion:

Although HSCT offers the only available cure for many diseases, the procedure remains limited by regimen-related toxicities, including GVD and hepatic VOD. Indeed, our results show a nearly four-fold higher mortality rate in patients with VOD compared with patients without VOD, and confirm previous observations.

In this study, prophylactic defibrotide reduced the incidence and severity of aGVHD. Damage to the endothelial cells of skin, gastrointestinal tract and liver from conditioning regimens contributes to the onset of aGVHD. Defibrotide's anti-inflammatory and protective effect on endothelial cells and down regulation of heparanase gene expression could explain these results, which appear highly consistent with the proposed mechanism of action of defibrotide.

Overall, defibrotide was well tolerated. Hemorrhages occurred with a similar frequency in both study arms, strongly suggesting that these events are more likely related to SCT and VOD than to the administration of defibrotide.

Object of the present invention is therefore defibrotide for use in prophylaxis and/or treatment of Graft versus Host Disease (GVHD) in humans, preferably in hematopoietic stem cell transplantation (HSCT), more preferably allogeneic hematopoietic stem cell transplantation. Graft versus Host Disease of the invention (GVHD) can be acute aGVHD and/or chronic cGVHD, preferably acute.

Defibrotide according to the invention can be administered before and/or after hematopoietic stem cell transplantation (HSCT), preferably before and/or after allogeneic hematopoietic stem cell transplantation.

Defibrotide according to the invention is preferably administered in a dose ranging from 10 to 60 mg/kg per day, preferably in a dose ranging from 20 to 40 mg/kg per day and more preferably in a dose of about 25 mg/kg per day; the kg refers to the body weight of the patient. According to the invention, defibrotide can be administered in a single or repeated dose/s per day, preferably in four (4) doses per day.

According to the invention defibrotide is preferably administered intravenously, more preferably is formulated in aqueous solution form.

REFERENCES

1. Copelan E A. Hematopoietic stem-cell transplantation. N Engl J Med 2006; 354(17):1813-26.
2. James L. M. Ferrara, M.D.a,*, John E. Levine, M.D.b, Pavan Reddy, M.D.c, and Ernst Holler, M.D.d Graft-versus-Host Disease. *Lancet*. 2009 May 2; 373(9674): 1550-1561
3. Stephanie J. Lee and Mary E. D. Flowers. Recognizing and Managing Chronic Graft-Versus-Host Disease Hematology 2008: 134-41
4. McDonald G B, Sharma P, Matthews D E, Shulman H M, Thomas E D. Venocclusive disease of the liver after bone marrow transplantation: diagnosis, incidence, and predisposing factors. Hepatology 1984; 4(1):116-22.
5. McDonald G B, Hinds M S, Fisher L D, et al. Venoocclusive disease of the liver and multiorgan failure after bone marrow transplantation: a cohort study of 355 patients. Ann Intern Med 1993; 118(4):255-67.
6. Coppell J A, Richardson P G, Soiffer R, et al. Hepatic veno-occlusive disease following stem cell transplantation: incidence, clinical course, and outcome. Biol Blood Marrow Transplant 2010; 16(2):157-68.
7. Eissner G, Multhoff G, Gerbitz A, et al. Fludarabine induces apoptosis, activation, and allogenicity in human endothelial and epithelial cells: protective effect of defibrotide. Blood 2002; 100(1):334-40.
8. Mitsiades C S, Rouleau C, Echart C, et al. Preclinical studies in support of defibrotide for the treatment of multiple myeloma and other neoplasias. Clin Cancer Res 2009; 15(4):1210-21.
9. Ostrovsky O, Shimoni A, Rand A, Vlodaysky I, Nagler A. Genetic variations in the heparanase gene (HPSE) associate with increased risk of GVHD following allogeneic stem cell transplantation: effect of discrepancy between recipients and donors. Blood 2010; 115(11):2319-28.
21. Echart C, Graziadio B, Somaini S, et al. The fibrinolytic mechanism of defibrotide: effect of defibrotide on plasmin activity. Blood Coagul Fibrinolysis 2009; 20(8):627-34.
22. Falanga A, Vignoli A, Marchetti M, Barbui T. Defibrotide reduces procoagulant activity and increases fibrinolytic properties of endothelial cells. Leukemia 2003; 17(8):1636-42.
30. Rowlings P A, Przepiorka D, Klein J P, et al. IBMTR severity index for grading acute graft-versus-host disease: retrospective comparison with Glucksberg grade Br J Haematol 1997 97(4):855-64.
31. Ruutu T, Barosi G, Benjamin R, et al. Diagnostic criteria for hematopoietic stem cell transplant-associated microangiopathy: results of a consensus process by an International Working Group. Haematologica 2007; January (92(1)):95-100.
35. Denne J S. Sample size recalculation using conditional power. Stat Med 2001; 20(17-18): 2645-60.
36. Tai B C, Machin D, White I, Gebski V. Competing risks analysis of patients with osteosarcoma: a comparison of four different approaches. Stat Med 2001; 20(5):661-84.
39. Ertault-Daneshpouy M, Leboeuf C, Lemann M, et al. Pericapillary hemorrhage as criterion of severe human digestive graft-versus-host disease. Blood 2004; 103(12): 4681-4.

TABLE 1

Baseline Demographics of the Study Participants.

| Variable | | Defibrotide Arm (N = 180) | Control Arm (N = 176) |
|---|---|---|---|
| Age - yr | Mean (SD) | 6.5 (5.2) | 6.7 (5.4) |
| | Median | 5.1 | 4.6 |
| | Range | <1-18 | <1-18 |
| Age category - No. (%) | Infant and toddlers (28 days to 2 years) | 46 (26) | 41 (23) |
| | Children (>2 and ≤11 years) | 91 (51) | 95 (54) |
| | Adolescents (>11 years) | 43 (24) | 40 (23) |
| Female gender - No. (%) | Female | 70 (39) | 75 (43) |
| Primary disease - No. (%) | Neuroblastoma | 34 (19) | 33 (19) |
| | Acute myelogenous leukemia | 31 (17) | 42 (24) |
| | Acute lymphoblastic leukemia | 26 (14) | 22 (13) |
| | Other leukemia | 8 (4) | 5 (3) |
| | Myelodysplastic syndrome | 20 (11) | 11 (6) |
| | Familial hemophagocytic lymphohistiocytosis | 6 (3) | 12 (7) |
| | Other inherited MAS | 4 (2) | 3 (2) |
| | Soft tissue sarcoma | 9 (5) | 8 (5) |
| | Osteopetrosis* | 7 (4) | 6 (3) |
| | Adrenoleukodystrophy | 1 (1) | 1 (1) |
| | Other | 34 (19) | 33 (19) |
| Type of donor - No. (%)† | Matched related donor | 35 (19) | 25 (14) |
| | Matched unrelated donor | 55 (31) | 61 (35) |
| | Mis-matched related donor | 14 (8) | 10 (6) |
| | Mis-matched unrelated donor | 18 (10) | 21 (12) |
| | Autologous HSCT | 53 (29) | 55 (31) |
| Type of graft - No. (%)† | Bone marrow | 79 (44) | 81 (46) |
| | Peripheral blood stem cells | 74 (41) | 77 (44) |
| | Umbilical cord blood | 16 (9) | 10 (6) |
| | T-cell depleted stem cells | 6 (3) | 4 (2) |
| Immunosuppression - No. (%) | ATG-Horse | 2 (1) | 2 (1) |
| | ATG-Rabbit | 65 (36) | 80 (45) |
| | Campath (alemtuzumab) | 9 (5) | 5 (3) |
| | Cyclosporine A | 100 (56) | 104 (59) |
| | Methotrexate | 56 (31) | 65 (37) |
| | OKT-3 | 11 (6) | 7 (4) |
| | Other‡ | 31 (17) | 28 (16) |
| Conditioning agent - No. (%) | Busulfan IV | 80 (44) | 81 (46) |
| | Busulfan PO | 46 (26) | 44 (25) |
| | Melphalan | 126 (70) | 114 (65) |
| | Cyclophosphamide | 84 (47) | 80 (45) |
| | Etoposide | 22 (12) | 25 (14) |
| | Total Body Irradiation | 17 (9) | 18 (10) |
| | Fludarabine | 34 (19) | 40 (23) |
| | Treosulfan | 13 (7) | 13 (7) |
| | Other§ | 34 (19) | 31 (18) |
| VOD high risk criteria - No. (%) | Second myeloablative transplant | 25 (14) | 23 (13) |
| | Allogeneic HSCT for leukemia | 17 (9) | 11 (6) |
| | Pre-existing liver disease | 41 (23) | 54 (31) |
| | Prior abdominal irradiation | 9 (5) | 8 (5) |
| | Prior treatment with gemtuzumab | 11 (6) | 5 (3) |
| | Conditioning with busulfan and melphalan | 106 (59) | 99 (56) |
| | Osteopetrosis | 7 (4) | 6 (3) |
| | Inherited MAS | 10 (6) | 15 (9) |
| | Adrenoleukodystrophy | 1 (1) | 1 (1) |

ATG denotes antithymocyte globulin, HSCT hematopoietic stem cell transplantation, MAS macrophage activation syndromes.
*Osteopetrosis was a stratification factor.
†Five patients (3%) in the defibrotide arm and 4 patients (2%) in the control arm were without transplant data (did not proceed to myeloablative transplant or withdrew conditioning before transplant).
‡Other immunosuppressants: mycophenolate mofetil, tacrolimus sirolimus, antilymphocyte globulin, prednisone/steroids, m-PDN and rituximab.
§Other conditioning agents: thiotepa, alemtuzumab, radioimmunoantibodym carboplatin, rituximab, ATG, clofarabine, Endoxan, dexamethasone, amsacrine, aracytabine, muromonab C and BCNU.

TABLE 2

Incidence of Veno-Occlusive Disease (VOD) Up To Day +30
Post Hematopoietic Stem-Cell Transplantation (HSCT).

| VOD Diagnosis | | Defibrotide Arm | Control Arm | P value |
|---|---|---|---|---|
| VOD by Day +30/IRC (ITT)* | VOD diagnosed - No./N (%) | 22/180 (12) | 35/176 (20) | |
| | Competing risk - % (95% CI)† | 13 (8, 19) | 20 (15, 27) | 0.05 |
| | Kaplan-Meier - % (95% CI) | 13 (9, 19) | 20 (15, 27) | 0.05‡ |
| VOD by Day +30/IRC (PP)§ | VOD diagnosed - No./N (%) | 18/159 (11) | 34/166 (20) | |
| | Competing risk - % (95% CI)† | 11 (7, 17) | 20 (15, 28) | 0.02 |
| | Kaplan-Meier - % (95% CI) | 11 (7, 18) | 21 (15, 28) | 0.02‡ |
| VOD in patients with osteopetrosis- No./N (%)¶ | | 1/7 (14) | 4/6 (67) | |
| VOD by type of donor - No. (%)* | Allogeneic HSCT | 15 (8) | 25 (14) | |
| | Autologous HSCT | 7 (4) | 10 (6) | |
| VOD diagnosis criteria met - No. (%)* | Weight gain >5% | 19 (11) | 30 (17) | |
| | Ascites | 17 (9) | 26 (15) | |
| | Hepatomegaly | 19 (11) | 30 (17) | |
| | Increased bilirubin | 13 (7) | 22 (13) | 0.09 |
| VOD by Age distribution No./N (%) | Infants | 9/46 (20) | 11/41 (27) | |
| | Children | 10/91 (11) | 16/95 (17) | |
| | Adolescents | 3/43 (7) | 8/40 (20) | |

*Intent to treat (ITT) population, N = 180 defibrotide arm and N = 176 control arm.
†Confidence interval (CI) by in transformation.
‡P value of log-rank test (from Kaplan-Meier estimator).
§Per protocol (PP) population, N = 159 defibrotide arm and N = 166 control arm.
¶N denotes number of patients with osteopetrosis; N = 7 defibrotide arm and N = 6 control arm.

TABLE 3

The Incidence of Acute and Chronic Graft-Versus-
Host disease (GVHD) in Allogeneic Hematopoietic
Stem-Cell Transplantation (HSCT) Patients.*

| GVHD classification | Defibrotide Arm (N = 122) No. (%) | Control Arm (N = 117) No. (%) | P value |
|---|---|---|---|
| Acute GVHD by Day +100 | 57 (47) | 76 (65) | 0.005† |
| Acute GVHD severity | | | |
| Grade 1 | 30 (25) | 33 (28) | 0.003‡ |
| Grade 2 | 18 (15) | 30 (26) | |
| Grade 3 | 5 (4) | 9 (8) | |
| Grade 4 | 4 (3) | 4 (3) | |
| Grades 2 to 4¶ | 27 (22) | 43 (37) | 0.01† |
| Chronic GVHD by Day +180 | 16 (13) | 17 (15) | 0.8§ |

*In the ITT population of all patients (allogeneic and autologous HSCT patients), acute GVHD was present in 32% (57/180) of patients in the defibrotide arm and 43% (76/176) of patients in the control arm; P = 0.03.
†P value from chi-square test for incidence of GVHD by Day +100.
‡P value from Wilcoxon test for grading of GVHD by Day +100.
§P value from chi-square test for incidence of GVHD by Day +180.
¶In a subset of grade 2 to 4 acute GVHD (excluding grade 1 mild cases), incidence was P = 0.01 and severity was P = 0.02 between the two arms.

TABLE 4

Veno-Occlusive Disease (VOD)-Associated Multiple
Organ Failure and Death Up To Day +100.*

| Event | Defibrotide Arm (N = 180) No. (%) | Control Arm (N = 176) No. (%) |
|---|---|---|
| Respiratory failure | 11 (6) | 15 (9) |
| Renal failure | 2 (1) | 10 (6) |
| Encephalopathy | 1 (1) | 3 (2) |
| Mortality | 4 (2) | 10 (6) |
| No organ failure or mortality | 169 (94) | 159 (90) |

*Composite score in patients with VOD: 1 point for each organ failure; 5 points for mortality.
Wilcoxon test for VOD-associated multiple organ failure and death in all patients at Day +100: defibrotide arm versus control arm, P = 0.03.
Wilcoxon test for VOD-associated multiple organ failure and death in patients with VOD at Day +30: defibrotide arm versus control arm, P = 0.2.

TABLE 5

Patients with Drug-Related Adverse Events According to Treatment
Arm by System Organ Class and Preferred Term.*

| System Organ Class/Abnormality | Defibrotide Arm (N = 177) No. (%) | Control Arm† (N = 176) No. (%) |
|---|---|---|
| Blood and lymphatic system disorders | | |
| Coagulopathy | 0 (0) | 1 (1) |
| Gastrointestinal disorders | | |
| Gastrointestinal hemorrhage | 2 (1) | 3 (2) |
| Abdominal pain | 1 (1) | 0 (0) |
| Diarrhea hemorrhagic | 1 (1) | 0 (0) |
| Hematemesis | 1 (1) | 0 (0) |
| Mouth hemorrhage | 1 (1) | 0 (0) |
| Nausea | 1 (1) | 0 (0) |
| Upper gastrointestinal hemorrhage | 0 (0) | 1 (1) |
| Vomiting | 1 (1) | 0 (0) |
| Investigations | | |
| Activated partial thromboplastin time prolonged | 0 (0) | 2 (1) |
| Prothrombin time prolonged | 1 (1) | 1 (1) |
| Respiratory, thoracic, and mediastinal disorders | | |
| Epistaxis | 2 (1) | 1 (1) |
| Hemothorax | 1 (1) | 1 (1) |
| Pulmonary hemorrhage | 0 (0) | 1 (1) |
| Vascular disorders | | |
| Hemorrhage | 1 (1) | 1 (1) |
| Microangiopathy | 0 (0) | 1 (1) |

*Related adverse events are those classified by the investigator as possibly, likely or certainly related to study drug.
†Adverse events reported following a diagnosis of veno-occlusive disease (VOD); defibrotide received as treatment for VOD.

The invention claimed is:

1. A method of preventing or alleviating graft versus host disease (GVHD) comprising identifying a patient at risk of developing GVHD, and administering to the patient an amount of defibrotide sufficient to reduce the occurrence or severity of GVHD.

2. The method of claim 1, wherein the GVHD is acute or chronic.

3. The method of claim 2, wherein the GVHD is acute.

4. The method of claim 1, wherein defibrotide is administered after a hematopoietic stem cell transplantation (HSCT).

5. The method of claim 4, wherein the HSCT is an allogenic hematopoietic stem cell transplantation.

6. The method of claim 1, wherein defibrotide is administered in a dose ranging from 10 to 60 mg/kg per day.

7. The method of claim 6, wherein defibrotide is administered in a dose ranging from 20 to 40 mg/kg per day.

8. The method of claim 7, wherein defibrotide is administered in a dose of about 25 mg/kg per day.

9. The method of claim 1, wherein defibrotide is administered in a single dose or in repeated doses per day.

10. The method of claim 9, wherein defibrotide is administered in four doses per day.

11. The method of claim 1, wherein defibrotide is administered intravenously.

12. The method of claim 1, wherein defibrotide is administered in an aqueous form.

13. The method of claim 1, wherein the defibrotide was obtained by extraction from animal and/or vegetable tissues.

14. The method of claim 13, wherein the defibrotide was obtained by extraction from mammalian organs.

* * * * *